(12) United States Patent
El-Hajal et al.

(10) Patent No.: US 10,386,657 B2
(45) Date of Patent: Aug. 20, 2019

(54) SYSTEM AND METHOD FOR OBTAINING LENS FABRICATION MEASUREMENTS THAT ACCURATELY ACCOUNT FOR NATURAL HEAD POSITION

(71) Applicant: Optikam Tech, Inc., Montreal (CA)

(72) Inventors: Bassem El-Hajal, Montreal (CA); Marco Lancione, Montreal (CA); Piotr Szymborski, Montreal (CA)

(73) Assignee: OptiKam Tech, Inc., Montreal, QC (CA)

( * ) Notice: Subject to any disclaimer, the term of this patent is extended or adjusted under 35 U.S.C. 154(b) by 69 days.

(21) Appl. No.: 15/588,645

(22) Filed: May 6, 2017

(65) Prior Publication Data

US 2018/0321517 A1 Nov. 8, 2018

(51) Int. Cl.
*A61B 3/10* (2006.01)
*A61B 3/00* (2006.01)
*G02C 13/00* (2006.01)
*A61B 3/11* (2006.01)

(52) U.S. Cl.
CPC .......... *G02C 13/005* (2013.01); *A61B 3/0025* (2013.01); *A61B 3/111* (2013.01)

(58) Field of Classification Search
CPC ..... A61B 3/0041; A61B 3/0025; A61B 3/111; A61B 3/112; A61B 2560/0223; A61B 2562/0247; A61B 2562/04; A61B 2562/046; A61B 2562/12; A61B 2562/164; A61B 3/0091; A61B 3/113; A61B 5/0002; A61B 5/0022; A61B 5/02055; A61B 5/02108; A61B 5/02125

USPC ........ 351/200, 204–206, 209–211, 221, 222, 351/223, 243–246
See application file for complete search history.

(56) References Cited

U.S. PATENT DOCUMENTS

| | | |
|---|---|---|
| 4,505,043 A | 3/1985 | Sztuka |
| 4,744,633 A | 5/1988 | Sheiman |
| 4,852,184 A | 7/1989 | Tamura et al. |
| 5,009,496 A | 4/1991 | Holton et al. |
| 5,365,286 A | 11/1994 | Masuda |
| 5,592,248 A | 1/1997 | Norton et al. |
| 6,508,553 B2 | 1/2003 | Gao et al. |
| 6,692,127 B2 | 2/2004 | Abitol et al. |
| 6,771,403 B1 | 8/2004 | Endo et al. |
| 7,001,020 B2 | 2/2006 | Yancey et al. |
| 7,062,454 B1 | 6/2006 | Giannini et al. |
| 7,648,236 B1 | 1/2010 | Dobson |
| 8,220,922 B2 | 7/2012 | Chaveau et al. |
| 8,857,986 B2 | 10/2014 | Fischer |

(Continued)

*Primary Examiner* — Brandi N Thomas
(74) *Attorney, Agent, or Firm* — LaMorte & Associates, P.C.

(57) ABSTRACT

A system and method for determining the measurements needed to fabricate prescription eyeglasses. The system and method take into account how the frames fit naturally on the head and how the person's posture orients the head and alters the line of sight through the lens of the eyeglasses. A sensor unit is provided that is attached to the eyeglass frames. The individual then wears the eyeglass frames and moves through at least one situational simulation. The sensor unit generates data that corresponds to changes in orientation. The data is used to determine how a person's line of sight is altered by the anatomy of the face and the posture of the head.

19 Claims, 5 Drawing Sheets

(56) References Cited

U.S. PATENT DOCUMENTS

| | | |
|---|---|---|
| 9,086,582 B1 | 7/2015 | Barton |
| 2010/0013739 A1 | 1/2010 | Sako et al. |
| 2013/0088490 A1 | 4/2013 | Rasmussen et al. |
| 2014/0104568 A1 | 4/2014 | Cuta et al. |
| 2014/0240470 A1 | 8/2014 | Dias Da Silva et al. |
| 2016/0299360 A1 | 10/2016 | Fonte et al. |
| 2017/0059886 A1* | 3/2017 | Fayolle .................. G02C 7/025 |

* cited by examiner

SYSTEM AND METHOD FOR OBTAINING LENS FABRICATION MEASUREMENTS THAT ACCURATELY ACCOUNT FOR NATURAL HEAD POSITION

BACKGROUND OF THE INVENTION

1. Field of the Invention

In general, the present invention relates to measurement systems and methods that are used to properly fit prescription eyewear. More particularly, the present invention relates to systems and methods that obtain measurements for fitting prescription eyewear that take into account the posture and head position of the person being fitted.

2. Prior Art Description

When a person gets a prescription for eyeglass lenses and selects a set of eyeglass frames, those lenses are not taken out of box, set into the frames, and handed to the customer. Rather, the lenses must be fabricated in a manner that takes into account the style of the selected eyeglass frames and the anatomical features of the person who will wear the eyeglass frames. When prescription lenses are fitted for a particular set of frames and for a particular person, several measurements must be made in order to ensure that the prescription lenses are fabricated properly. Many of the measurements depend solely upon the style and model of the eyeglass frames being considered. Other measurements depend upon the anatomy of the person being fitted. Still other measurements depend upon how the eyeglass frames sit upon the face when being worn in a normal manner. For instance, the distance between a person's eyes varies from person to person. Furthermore, the shape and slant of a person's nose varies from person to person. The size and slant of the nose determines how far down the face a set of eyeglass frames will come to rest in front of the eyes. This determines what portions of the lenses are positioned in front of the pupils when a person looks straightforward. Accordingly, the way the lenses in the frames rest upon the face is a significant variable in how the lenses should be fabricated.

In addition to a person's facial anatomy, the position of the head and the posture of the body also have significant effects on the proper fitting of eyeglasses. Few people have a fully erect posture and view their environment by only looking straight ahead. Rather, most people have a slight slouch. Furthermore, most people look slightly downward as they walk or when they sit. Some people also have a tendency to tilt their head to one side or another as they drive or read. Each one of these head positions causes a person to view through a slightly different section of the lenses in a set of eyeglasses.

In order to properly create the lenses for a set of eyeglasses, the optician typically determines the center of the wearer's pupils relative the eyeglass frames to be worn. The lens lab then grinds the lenses using the measured pupil centers as the center of curvature for the lenses. Often the optician marks the center of the wearer's pupils on the lenses, as that person is erect and facing forward. This is an unnatural position. Consequently, when the lenses are fabricated and set into the eyeglass frames, a wearer may spend most of the time looking through a section of the lenses that are off-center. The consequence is that the light diffractions created by the lenses are not optimized to the center of the pupils. The eyeglasses, therefore, do not create as clear of an image as they could.

In the prior art, there are systems that are used to help a lens fabricator determine the measurements needed to properly fabricate prescription lenses. However, many of these systems are bulky devices that mount to the eyeglass frames in front of the eyes. Such prior art systems are exemplified by U.S. Pat. No. 8,857,986, to Fischer. The problem with such prior art systems is that they capture data from only one posture of the head. That is, the optician records data from the device while standing next to the person wearing the device. When the optician stands near a person to take a pupil measurement or a photograph, that person often assumes a posture and head position that is different from his/her natural posture. The result is that the person will not wear the eyeglasses while maintaining a normal posture as the measurements are taken. The results are measurements that contain false normals. This can result in lenses that are less than optimal when worn in an ordinary manner.

A need therefore exists for a system and method that can be used to determine the measurements needed to accurately fabricate prescription lenses by determining changes in line of sight causes by face anatomy and head posture. This need is met by the present invention as described and claimed below.

SUMMARY OF THE INVENTION

The present invention is a system and method for determining the measurements needed by a lens fabricator to correctly fit prescription eyeglasses to an individual. The system and method take into account how the frames fit naturally on the head and how the person's posture orients the head alters the line of sight through the lens of the eyeglasses. The individual first selects eyeglass frames into which the prescription lenses are to be set. A sensor unit is provided that is attached to the eyeglass frames. The individual then wears the eyeglass frames. With the sensor unit attached, an individual moves through at least one situational simulation, such as walking, standing, sitting or reading. The situational scenario is selected based upon the lifestyle and typical activities of the individual being measured. The sensor unit generates data that corresponds to changes in orientation experienced during the situational simulation.

Measurements are taken that reference the eyeglass frames and how the eyeglass frames rest on the face of the individual. The measurements can be taken directly or can be taken from images of the individual wearing the eyeglass frames. The data collected by the sensor unit can be used to determine how a person's line of sight is altered by the anatomy of face and the posture of the head. The data collected by the sensor unit is processed and is used to alter the measurements, therein producing a final set of measurements. The final set of measurements is used to fabricate the prescription glasses.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

The present invention system and method can be used to determine measurements needed to accurately fabricate prescription lenses. The prescription lenses can be used with many different shapes and models of eyeglasses, sunglasses, and safety glasses. However, only one exemplary embodiment of eyeglass frames is illustrated. This embodiment is exemplary and is intended to represent most all models and styles of eyeglass and sunglass frames. Accordingly, the model and style of the eyeglass frames in the exemplary embodiment is presented for education and discussion and should not be considered a limitation in the interpretation of the appended claims.

Figure 1:
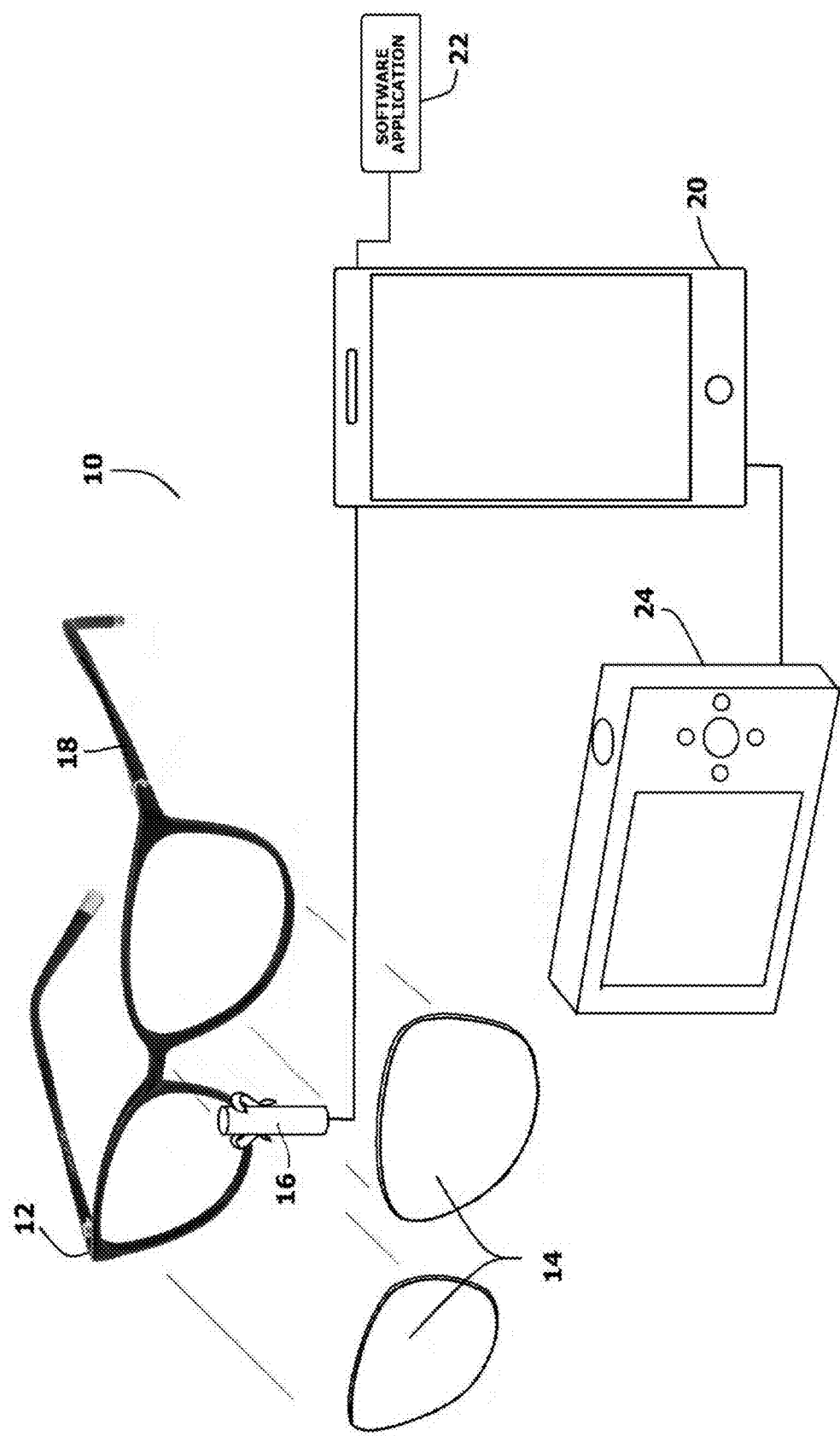
FIG. 1 shows the hardware of the present invention system.

Referring to FIG. 1, a measurement system 10 is provided that is used to generate all the measurements that are needed to properly fabricate prescription lenses for a particular person. The measurement system 10 begins with the eyeglass frames 12 to which the prescription lenses 14 are to be fitted. The eyeglass frames 12 are selected by a user and are worn by the user.

A sensor unit 16 is provided. The sensor unit 16 has the ability to measure a pitch angle relative to a reference plane. The sensor unit 16 is lightweight and temporarily mounts to the eyeglass frames 12. The sensor unit 16 collects and transmits pitch angle data to a computer device 20. The computer device 20 can be a personal computer, laptop computer, a tablet, and/or a server that accessible through a data network. In the preferred embodiment, the computer device 20 is a smart phone that is running a customized software application 22. The data can be transmitted to the computer device 20 using a wire, or using any wireless data transmission protocol, such as Bluetooth®.

In addition to the sensor unit 16 and the computer device 20, the present invention measurement system 10 may require the use of images gathered from a camera 24. The camera 24 can be a camera integrated into the computer device 20, such as a cell phone camera. However, a separate digital camera can also be used. If a separate camera 24 is used, the measurement system 10 has the ability to transfer digital images from the camera 24 to the computer device 20.

Figure 2:
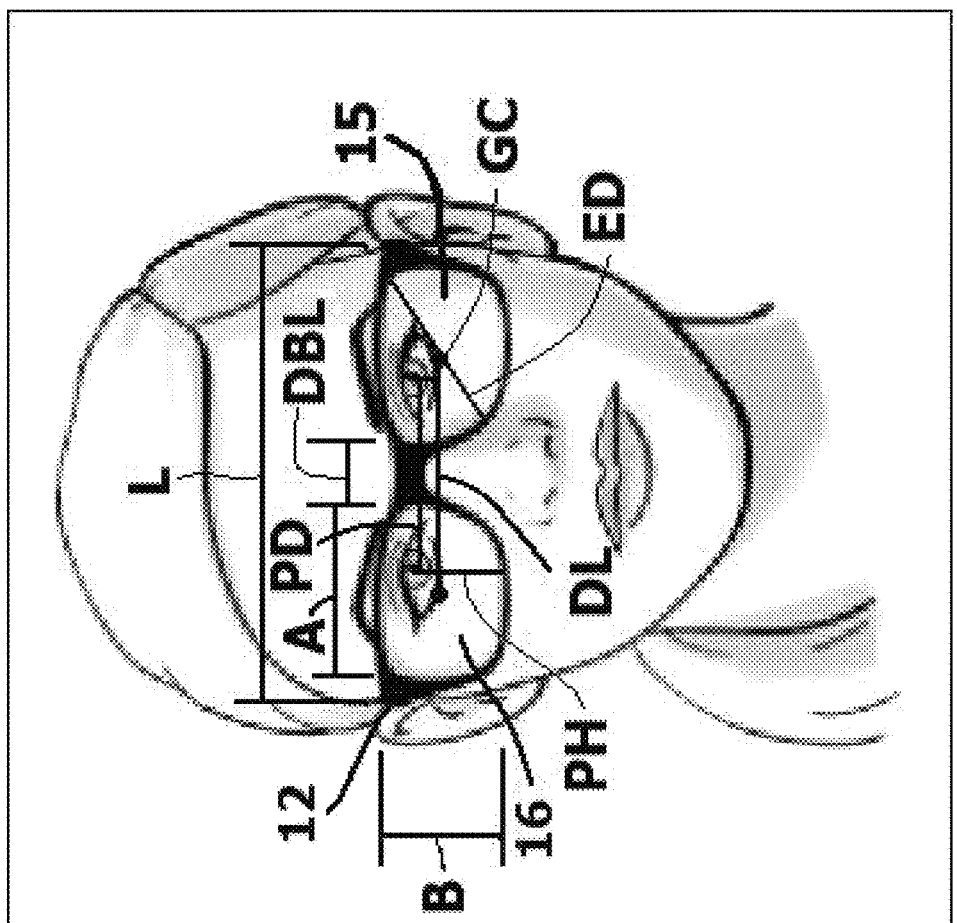
FIG. 2 is a front image of an individual wearing eyeglass frames, wherein the image indicates the variables needed to be known for the proper fabrication of prescription lenses.
Figure 3:
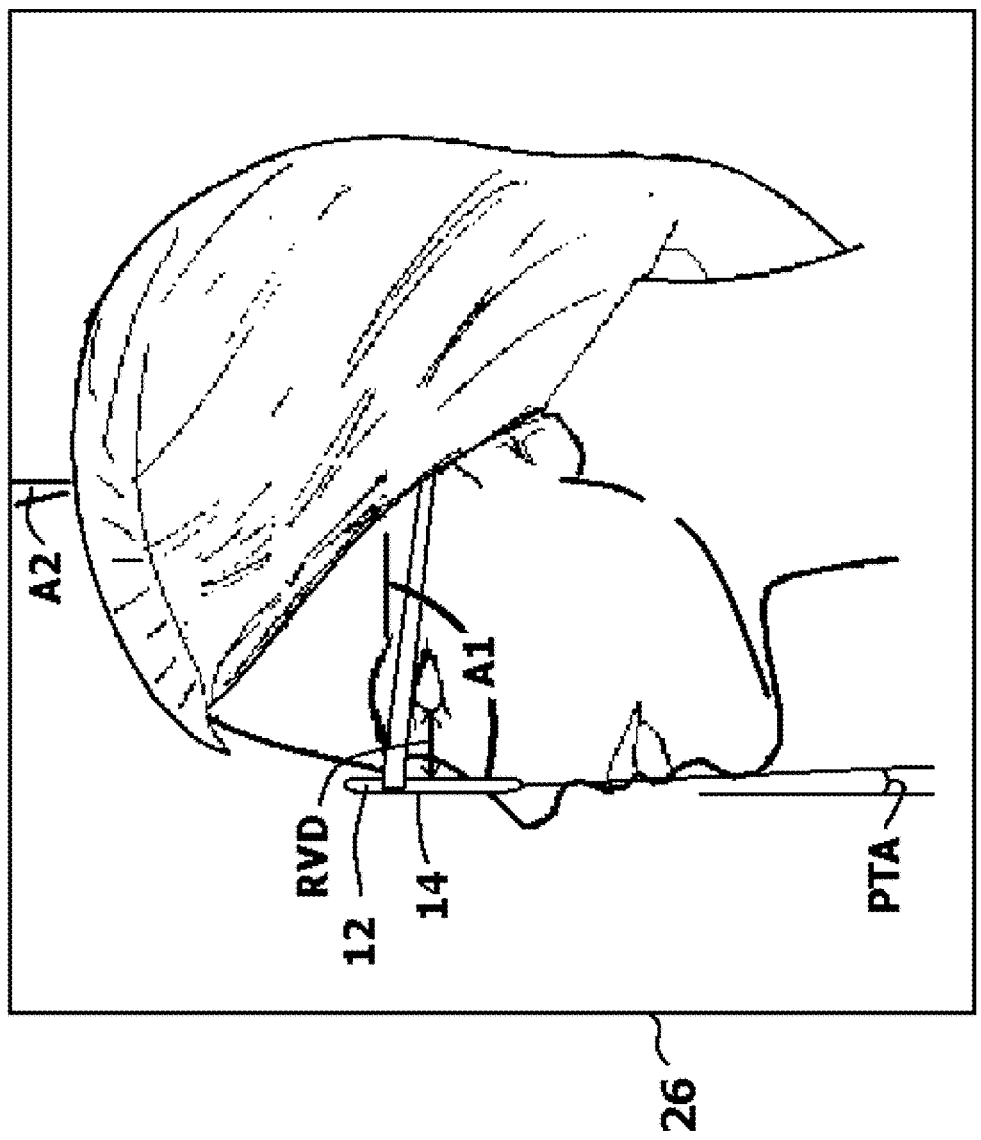
FIG. 3 is a side view of an individual wearing eyeglass frames and indicating some variables needed for the proper fabrication of prescription lenses.

Referring to FIG. 2 and FIG. 3 in conjunction with FIG. 1, it will be understood that in order to properly fabricate a set of prescription lenses 14, the physical dimensions of the eyeglass frames 12 need to be known. In addition, certain measurements need to be taken from the eyeglass frames 12 that reference the anatomy of the eyes and face. Collectively, all of the major variables that are needed to properly fabricate a set of prescription eyeglasses are present in Table 1, below.

TABLE 1

| Frame Dimension Variables | |
|---|---|
| A | Lens Length |
| B | Lens Height |
| ED | Effective Diameter |

TABLE 1-continued

| | |
|---|---|
| GC | Geometrical Centers |
| DL | Datum Line |
| L | Frame Length |
| DBL | Distance Between Lenses |
| Anatomical Dependent Variables | |
| PH | Pupil Height |
| PD | Pupil Distance |
| PTA | Pantoscopic Tilt Angle |
| RVD | Rear Vertex Distance |

FIG. 2 is a front image 25 of a person wearing eyeglass frames 12. FIG. 3 is a side image 26 of the same. The eyeglass frames 12 have lens openings 15 which are designed to hold the prescription lenses 14. Referring to Table 1 in conjunction with FIG. 2 and FIG. 3, it will be understood that each model and style of eyeglass frames 12 has its own critical dimensions that need to be known in order to shape the prescription lenses 14 for the eyeglass frames 12. Those measurement variables include the overall shape of the eyeglass frames 12. Eyeglass frames 12 hold lenses 14 in a lens plane. Typically, the lens plane associated with a set of eyeglasses frames 12 is at a slight angle relative to the vertical. This tilt angle A1 is sometimes referred to as the "device panto" in the industry. The tilt of the lens plane is also affected by the tilt angle A2 of the person's head. This tilt angle A2 is caused by posture and the way a person holds his/her head.

Within the overall shape of the eyeglass frames 12, there are the lens length "A" and the lens height "B". There is the effective diameter "ED" as measured through the geometric center "GC" of each lens 14. The geometric centers "GC" of both lenses 14 align horizontally on the datum line "DL". The distance between the geometric centers "DBC" is the distance between the geometric centers "GC" in the horizontal plane. The frame length "L" is the distance between temples in the horizontal plane. The bridge size, or distance between lenses 14 "DBL" is the minimum distance between the left and right lenses 14. The pantoscopic tilt angle "PTA" corresponds to the total tilt of the lens plane. the proper pantoscopic tilt angle "PTA" for an individual is highly dependent upon the natural head posture of that individual. This is because the vertical plane is a constant and any downward tilt of the head directly changes the tilt of the eyeglasses frames 12 relative the vertical plane. As such, the pantoscopic tilt angle "PTA" is the sum of the tilt angle A1 caused by the device panto plus the tilt angle A2 cause by head posture.

Other measurements that depend upon the anatomy of the person wearing the eyeglass frames 12 include pupil height "PH", pupil distance "PD", and rear vertex distance "RVD". The pupil height "PH" is the measured height of the pupils above the bottom of the lens 14. The pupil distance "PD" is the distance between pupils in the horizontal plane. The rear vertex distance "RVD" is the gap distance between the pupil and the lens 14.

The pantoscopic tilt angle "PTA", pupil height "PH" and the rear vertex distance "RVD" are measurements that depend upon how the prescription lens 14 are held in front of the eyes. They also depend upon how a person normally orients his/her head when looking through the prescription lens 14. The measurements of Table 1 are readily obtained from images of the prescription eyeglasses 12 being worn. For example, all the variables of Table 1 can be obtained from images provided at least one of the measurement variables is known and can be used as a reference scale.

Alternately, some of the variables can be measured using prior art measuring devices, such as the prism device disclosed in U.S. Pat. No. 8,857,986 to Fischer.

What is not known is how much the user changes the orientation of his/her head when they read, drive, stand, walk, watch television, or otherwise perform ordinary tasks while wearing eyeglasses. Referring to FIG. 3, it can be seen that if a person has a slight slouch or downward head inclination, the tilt angle A2 affects the overall pantoscopic tilt angle "PTA" of the eyeglass frames 12 when worn. Variations to the pantoscopic tilt angle "PTA", can also affect pupil height "PH" and rear vertex distance "RVD". All three affect the line of sight through the lenses 14.

Figure 4:
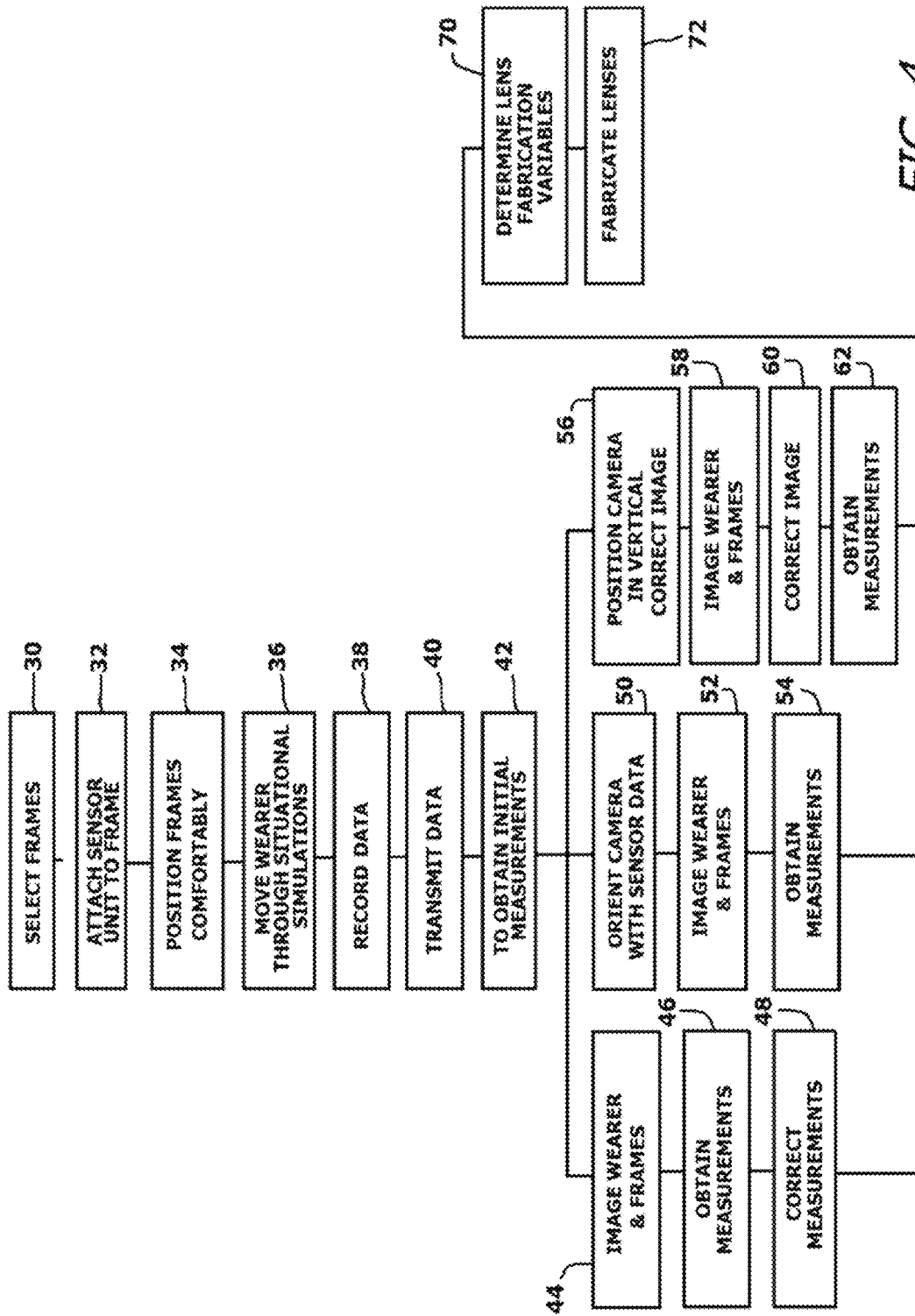
FIG. 4 is block diagram showing the methodology of the present invention system.

Referring to FIG. 4 in conjunction with FIG. 1, FIG. 2 and FIG. 3, the details of the operation of the present invention measurement system 10 is described. In order to utilize the measurement system, a set of eyeglass frames 12 is first selected. See Block 30. The sensor unit 16 is attached to the eyeglass frames 12. See Block 32. The wearer is instructed to wear the eyeglass frames 12 in a comfortable position. See Block 34. The wearer is then asked to participate in a situational simulation. See Block 36. If the wearer typically wears eyeglasses when sitting at a desk, the wearer is asked to sit at a desk. If the wearer typically wears eyeglasses when walking, the wearer is asked to walk. Similar situational simulations can be practiced for other activities, such as standing, reading and like. What is of importance is that the wearer wears the eyeglass frames 12 in the same manner as they would in real life. Likewise, the wearer places his/her body in the same position and holds his/her head in the same manner as they would in everyday life. Accordingly, the overall pantoscopic tilt angle "PTA" is true to everyday life.

During the performance of the situational simulations, the sensor unit collects positional data that identifies the changes in pantoscopic tilt angle "PTA" experienced by the eyeglass frames 12. See Block 38. The data is transmitted to the computer device 20 that runs the operational software application 22. See Block 40. The software application 22 then determines what pantoscopic tilt angle "PTA" represents the average posture of the user during a given activity.

Once the data that identifies the natural posture of the person is identified, some physical reference data can be obtained. See Block 42. The dimensions of the eyeglass frames 12 can be retrieved by the computer device 20 using the running application software 22. The application software 22 can access remote databases that store physical dimensions for various makes and models of eyeglass frames 12. If the dimensions of the eyeglasses frames 12 are unknown, the dimensions can be obtained directly from the eyeglass frames 12. Alternatively, the eyeglass frames 12 can be imaged while being worn using the camera 24. Measurements can be obtained by taking scaled measurements from the acquired images.

With the dimensions of the eyeglass frames 12 known and the average pantoscopic tilt angle "PTA" known, a corrected line of sight for a particular wearer can be produced. This can be done using one of three options. Referring to Block 44, a first option is discussed. In this option, one or more images of the wearer and the eyeglass frames 12 are taken using the camera 24. Initial measurements are taken from the images. See Block 46. The initial images are then corrected with the data from the sensor regarding the average pantoscopic tilt angle "PTA". This produces a final set of measurements. See Block 48.

Referring to Block 50, a second option is discussed. In this option, the camera 24 is positioned in front of the wearer at an angle that compensates for the average pantoscopic tilt angle "PTA" obtained from the sensor data. This is best done if the camera being used is part of the computer device 20, such as with a Apple iPad® tablet. In such a case, software application 22 running in the computer device 20 can instruct a user in the proper orientation of the camera. Once properly oriented, one or more images of the wearer and the eyeglass frames 12 can be taken. See Block 52. Measurements can be taken from the images, wherein the adjustment for the average pantoscopic tilt angle "PTA" is inherent in the images. See Block 54.

Referring to Block 56, a third option is discussed. In this option, the camera 24 is positioned in front of the wearer in the vertical plane. This is best done if the camera being used is part of the computer device 20, such as with a Apple iPad® tablet. In such a case, software application 22 running in the computer device 20 can automatically correct any image obtained by the camera in real time using the offset angles for the average pantoscopic tilt angle "PTA" that were collected by the sensor unit 16. See Block 58 and Block 60. In final measurements are then obtained from the corrected image. See Block 62.

Figure 5:
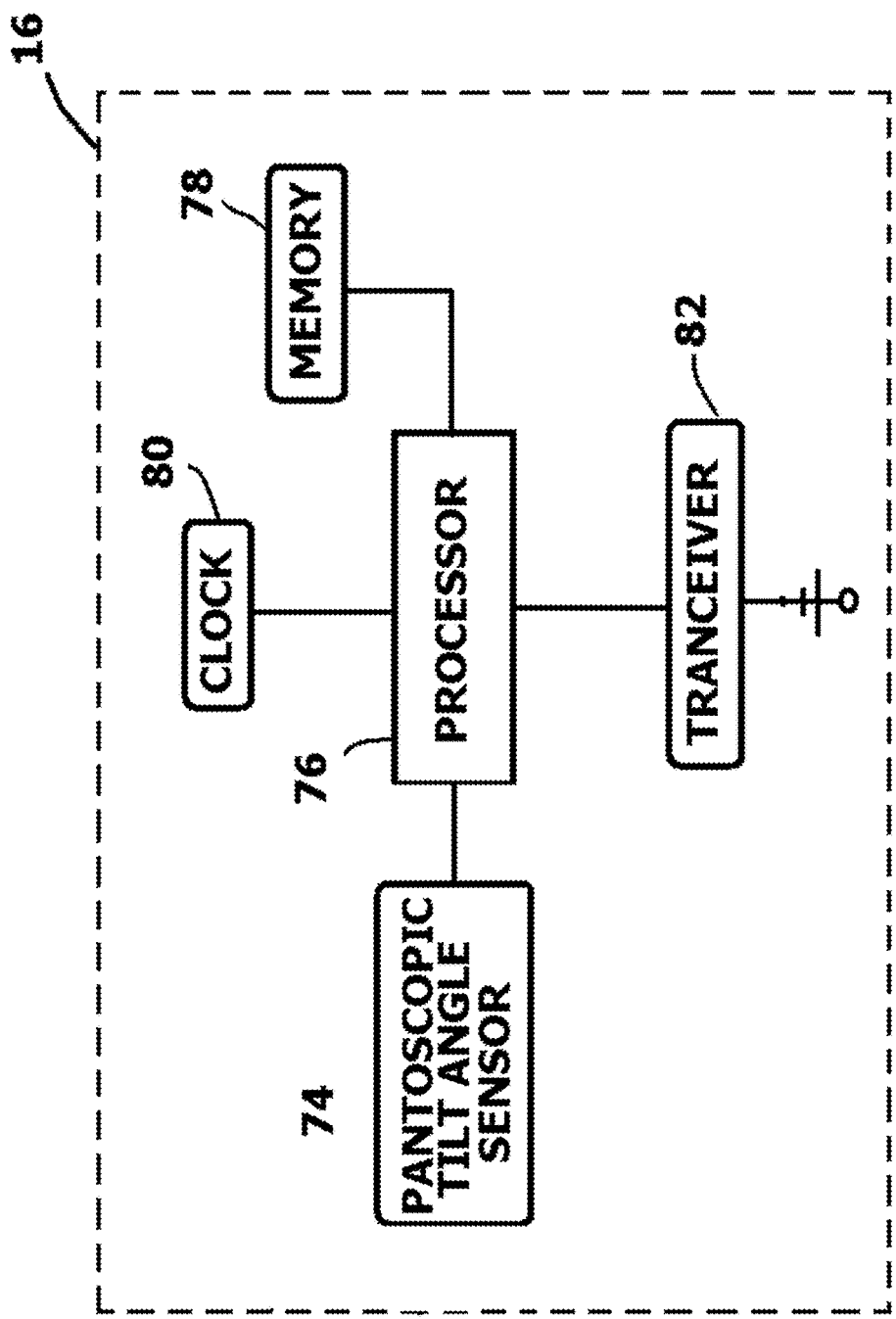
FIG. 5 is a schematic of the sensor unit used as part of the present invention system.

Referring to FIG. 5, it can be seen that the sensor unit 16 includes a pantoscopic tilt angle sensor 74. The sensor 74 produces data that corresponds to the pantoscopic tilt angle of the sensor unit 16 as it moves with the eyeglass frames 12. The angle data is read to a processor 76 that stores the data in a memory 78. A clock 80 is provided so that the angle data is time referenced. This enables the different values of angle data to be sorted by time of occurrence, duration, and frequency. The processor 76 transmits the data to the computer device 20 when properly queried by the computer device 20. If the angle data is transferred wirelessly, the sensor unit 16 also includes a transceiver 82, so that it can receive wireless commands from the computer device 20 and can transmit data to the remote computer device 20.

Returning to FIG. 4 in conjunction with FIG. 1, FIG. 2 and FIG. 3, it will be understood that the software application 22 being run by the computer device 20 receives angle data transmitted by the sensor unit 16. The running software application 22 processes the angle data and isolates the data that corresponds to when the wearer was sitting, reading, walking or otherwise performing an everyday task where they need their eyeglasses. The software application 22 reads the data and compiles an average value for the pantoscopic tilt angle. Using the acquired angle data, the software application 22 modifies the initial measurements in one of the three optional manners previously described. The pantoscopic tilt angle embodies the variations caused by slouching, head tilt, and nose contact position. Accordingly, the modified measurements represent the best average orientation in which the eyeglass frames 12 and prescription lenses 14 will be worn by a particular user. All the variables listed in Table A are now calculable. See Block 70.

Once all the variables listed in Table A become known, proper prescription lenses 14 can be fabricated for the eyeglass frames 12. See Block 72. The prescription lenses 14 are not only properly crafted for magnification, but are customized for how the eyeglass frames 12 hold the lenses 14 in front of the customer's eyes.

It will be understood that the exemplary embodiment of the present invention system that is illustrated is merely exemplary and that many aspects of the system can be redesigned in manners that are functionally equivalent. All such variations, modifications and alternate embodiments are intended to be included within the scope of the present invention as claimed.

What is claimed is:

1. A method of obtaining measurements needed to correctly fabricate prescription lenses for an individual, said method comprising the steps of:
   providing eyeglass frames into which said prescription lenses are to be set;
   providing a sensor unit that is separate and distinct from said eyeglass frames, wherein said sensor unit contains a detects changes in orientation of said sensor unit;
   temporarily attaching said sensor unit to said eyeglass frames;
   placing said sensor unit and said eyeglass frames on the individual, while the individual moves through at least one situational simulation, wherein said eyeglass frames have a pantoscopic tilt angle when worn that changes during said at least one situational simulation, wherein said sensor unit generates data corresponding to said changes in pantoscopic tilt angle;
   taking initial measurements needed to fabricate said prescription lenses from said eyeglass frames and from said individual;
   altering said initial measurements with said data to produce a final set of measurements; and
   fabricating said prescription lenses using said final set of measurements.

2. The method according to claim 1, wherein providing a sensor unit includes providing a sensor that detects changes in an orientation angle caused by changes in posture.

3. The method according to claim 1, further including providing a computer device, and having said sensor unit transmit said data to said computer device.

4. The method according to claim 3, wherein said sensor unit transmits said data to said computer device using a wireless transmission.

5. The method according to claim 1, further including imaging said individual wearing said eyeglass frames to obtain reference images.

6. The method according to claim 5, wherein said initial measurements are obtained from said reference images.

7. The method according to claim 1, wherein said at least one situational simulation is selected from a group consisting of standing, looking at a distant point, sitting and reading.

8. A method of obtaining measurements needed to correctly fabricate prescription lenses for an individual, said method comprising the steps of:
   providing eyeglass frames into which said prescription lenses are to be set;
   providing at least one sensor that is separate and distinct from said eyeglass frames;
   attaching at least one sensor to said eyeglass frames wherein said at least one sensor detects changes in orientation of said eyeglass frames including changes in pantoscopic tilt angle;
   wearing said eyeglass frames with said at least one sensor while performing a situational simulation, wherein said at least one sensor generates data that corresponds to said changes in orientation experienced during said situational simulation;
   obtaining initial measurements that reference said eyeglass frames needed to fabricate said prescription lenses for said eyeglass frames;
   altering said initial measurements with said data to produce a final set of measurements.

9. The method according to claim 8, wherein said final set of measurements include measurements for pupil height, and rear vertex distance, as well as said pantoscopic tilt angle.

10. The method according to claim 8, wherein obtaining initial measurements includes physically measuring variables that reference said eyeglass frames while said eyeglass frames are being worn.

11. The method according to claim 8, wherein obtaining initial measurements includes imaging said eyeglass frames being worn and obtaining said initial measurements from images.

12. The method according to claim 8, wherein said eyeglass frames have lens openings and attaching at least one sensor to said eyeglass frames includes attaching said at least one sensor to said eyeglass frames.

13. The method according to claim 12, wherein said at least one sensor is part of a sensor unit that contains a processor and a clock circuit.

14. The method according to claim 13, further including providing a computer device, and having said sensor unit transmit said data to said computer device.

15. The method according to claim 14, wherein said sensor unit transmits said data to said computer device using a wireless transmission.

16. A method of obtaining measurements needed to correctly fabricate prescription lenses, said method comprising the steps of:
   providing eyeglass frames having lens openings into which said prescription lenses are to be set;
   attaching at least one sensor to said eyeglass frames that detects changes in orientation of said eyeglass frames including tilt angle relative to a vertical plane;
   wearing said eyeglass frames with said at least one sensor for a period of time, wherein said at least one sensor generates data that corresponds to said changes in orientation experienced during said period of time; and
   utilizing said data to generate at least some final measurements sufficient to fabricate said prescription lenses.

17. The method according to claim 16, further including obtaining initial measurements that reference said eyeglass frames and altering said initial measurements with said data to produce a full set of final measurements sufficient to fabricate said prescription lenses.

18. The method according to claim 16, wherein utilizing said data to generate at least some final measurements includes determining a pantoscopic tilt angle from said data and imaging a person wearing said eyeglass frames with a camera that is angled to compensate for said pantoscopic tilt angle, wherein said camera capture at least one image.

19. The method according to claim 18, wherein at least some of said final measurements are taken from said at least one image.

* * * * *